United States Patent

Rühl et al.

[11] Patent Number: 5,936,126
[45] Date of Patent: Aug. 10, 1999

[54] PROCESS FOR REACTING AN ORGANIC COMPOUND IN THE PRESENCE OF A SUPPORTED RUTHENIUM CATALYST

[75] Inventors: Thomas Rühl, Frankenthal; Boris Breitscheidel, Limburgerhof; Jochem Henkelmann, Mannheim; Wolfgang Reif, Frankenthal; Helmuth Menig, Friedelsheim; Sabine Weiguny, Freinsheim, all of Germany

[73] Assignee: BASF Aktiengesellschaft, Ludwigshafen, Germany

[21] Appl. No.: 08/877,819

[22] Filed: Jun. 18, 1997

[30] Foreign Application Priority Data

Jun. 19, 1996 [DE] Germany .......................... 196 24 484
Jan. 22, 1997 [DE] Germany .......................... 197 02 103

[51] Int. Cl.$^6$ .................................................. C07C 209/72
[52] U.S. Cl. ........................ 564/451; 564/450; 568/816; 568/831; 568/862; 568/863
[58] Field of Search .................................. 568/834, 816, 568/862, 863, 831; 564/450, 451

[56] References Cited

U.S. PATENT DOCUMENTS

| | | |
|---|---|---|
| 2,456,428 | 12/1948 | Parker . |
| 2,585,583 | 2/1952 | Pinkney . |
| 2,606,925 | 8/1952 | Whitman . |
| 2,647,146 | 7/1953 | Arthur, Jr. . |
| 2,822,392 | 2/1958 | Illich et al. . |
| 2,927,127 | 3/1960 | Somerville . |
| 3,122,526 | 2/1964 | Schuller . |
| 3,520,928 | 7/1970 | Greco . |
| 3,591,635 | 7/1971 | Farrissey, Jr. . |
| 3,636,108 | 1/1972 | Brake . |
| 3,697,449 | 10/1972 | Brake . |
| 3,966,833 | 6/1976 | Cosyns et al. ........................... 260/672 |
| 4,343,955 | 8/1982 | Oshima et al. . |
| 4,371,612 | 2/1983 | Matsumoto et al. . |
| 4,424,162 | 1/1984 | Rosen ..................................... 260/409 |
| 4,429,155 | 1/1984 | Goetz et al. . |
| 4,551,564 | 11/1985 | Otte et al. . |
| 4,914,239 | 4/1990 | Kiyuma et al. . |
| 4,952,549 | 8/1990 | Immel et al. . |
| 5,110,779 | 5/1992 | Hucul . |
| 5,322,965 | 6/1994 | Immel et al. . |
| 5,773,657 | 6/1998 | Ruetter et al. .......................... 564/450 |
| 5,856,590 | 1/1999 | Emura et al. ........................... 568/835 |

OTHER PUBLICATIONS

*Chem. Abst.*, vol. 70, An 11218Y, 1969 (=JP 43 003 180).
Derwent Abst. 95–341826 (=JP 7235424) 1995.
Derwent Abst. 84–315129 (=JP 59196843) 1984.
Derwent Abst. 70 240P (=DE 1226303) 1970.
Derwent Abst. 735306U (=DE 2132547) 1973.
Abstract of PL 137526 1981.

*Primary Examiner*—Brian M. Burn
*Attorney, Agent, or Firm*—Keil & Weinkauf

[57] ABSTRACT

A process for the hydrogenation of an aromatic compound, in which at least one hydroxyl group is attached to an aromatic core, or an aromatic compound, in which at least one amino group is attached to an aromatic core, in the presence of a catalyst containing, as active metal, ruthenium and optionally one or more other Group IB, VIIB, or VIIIB metals, applied to a macroporous support.

8 Claims, No Drawings

PROCESS FOR REACTING AN ORGANIC COMPOUND IN THE PRESENCE OF A SUPPORTED RUTHENIUM CATALYST

The present invention relates to a process for reacting an organic compound in the presence of a catalyst which comprises ruthenium and optionally one or more further Group IB, VIIB, or VIIIB metals, applied to a macroporous support, as active metal.

In one embodiment the present invention relates to a process for the reaction, preferably hydrogenation, of an aromatic compound in which at least one hydroxyl group is attached to an aromatic core, where preferably at least one optionally substituted $C_1$–$C_{10}$- alkyl group and/or at least one $C_1$–$C_{10}$-alkoxy group is attached to an aromatic core in addition to said at least one hydroxyl group. Furthermore, monoalkyl-substituted phenols are preferably used in the process of the invention.

The mononuclear or polynuclear aromatic compounds are preferably hydrogenated in the presence of the catalyst that is described herein to produce the corresponding cycloaliphatic compounds, during which process the hydroxyl group remains intact.

Cycloaliphatic alcohols, and particularly alkylcyclohexanols, are important intermediates for the preparation of various perfumes, medicines and other organic fine chemicals. The above cycloaliphatic alcohols are readily obtained by catalytic hydrogenation of the corresponding aromatic precursors.

The method of preparing alkylcyclohexanols by catalytic hydrogenation of the corresponding alkylphenols is known. The hydrogenation of alkylphenols to form the corresponding alkylcyclohexanols in the presence of hydrogenation catalysts, particularly catalysts that are applied to supports, has been described in many places.

The catalysts used are metallic rhodium, rhodium/platinum and rhodium/ruthenium alloys, and also ruthenium, palladium, or nickel on catalyst supports. The catalyst supports used are carbon, barium carbonate, and, particularly, aluminum oxide.

PL 137,526 describes the hydrogenation of p-tert-butylphenol to form p-tert-butylcyclohexanol using a nickel catalyst.

DE-A 3,401,343 and EP 0,141,054 describe a process for the preparation of 2- and 4-tert-butylcyclohexanol from 2- and 4-tert-butylphenol by catalytic hydrogenation. The hydrogenation is carried out in two stages, a palladium catalyst on a $Al_2O_3$ support being used in the first stage and a ruthenium catalyst on a $Al_2O_3$ support being used in the second stage. The metal content on the support is from 0.1 to 5 wt.-%. The supports are not specified. The process is carried out under a pressure of 300 bar with recycling of the product, and there are preferably obtained the cis-tert-butylphenols, during which process from 0.1 to 0.5% of by-products are formed.

U.S. Pat. No. 2,927,127 describes a process for the preparation of p-tert-butylcyclohexanol and esters thereof by catalytic hydrogenation of p-tert-butylphenol. The catalysts used are 5% of rhodium on carbon, 5% of palladium on barium carbonate and 5% of ruthenium on carbon. When using ruthenium on carbon the process has been carried out under a pressure of from 70 to 120 bar and at a temperature of from 74° C. to 93° C. The hydrogenation product obtained comprised 66% of cis-isomer.

DE-A 2,909,663 describes a process for the preparation of cis-alkylcyclohexanols by catalytic hydrogenation of the corresponding alkylphenols. The catalyst used was ruthenium on a $Al_2O_3$ support. The process was carried out under pressures of 40, 60, and 80 bar. The products obtained were predominantly cis-alkylcyclohexanols, whilst the by-product obtained comprised from 0.1 to 1% of alkyl benzenes.

In a further embodiment the present invention relates to a process for the reaction, preferably hydrogenation, of an aromatic compound in which at least one amino group is attached to an aromatic core, where preferably at least one optionally substituted $C_1$–$C_{10}$ alkyl group and/or at least one $C_1$–$C_{10}$ alkoxy group is attached to an aromatic core in addition to said at least one amino group. In particular, monoallyl-substituted amines are preferably used.

The mononuclear or polynuclear aromatic compounds are preferably hydrogenated to the corresponding cycloaliphatic compounds in the presence of the catalyst that is described herein, during which process the amino group remains intact.

Cycloaliphatic amines, and particularly optionally substituted cyclohexylamines and dicyclohexylamines, are used for the preparation of age protectors for caoutchoucs and plastics materials, as anticorrosive agents and also as intermediates for plant protectants and textile auxiliaries. Moreover cycloaliphatic diamines are used in the manufacture of polyamide and polyurethane resins and are also used as curing agents for epoxy resins.

It is known to be possible to prepare cycloaliphatic amines by catalytic hydrogenation of the corresponding mononuclear or polynuclear aromatic amines. The hydrogenation of aromatic amines to form the corresponding cycloaliphatic amines in the presence of hydrogenation catalysts, particularly catalysts that are applied to supports, has been described in many places.

The catalysts used are for example Raney cobalt containing basic additives (JP 43/3180), nickel catalysts (U.S. Pat. No. 4,914,239, DE 805,518), rhodium catalysts (BE 739,376, JP 7,019,901, JP 7,235,424), and also palladium catalysts (U.S. Pat. No. 3,520,928, EP 501,265, EP 53,818, JP 59/196843). In most cases, however, catalysts containing ruthenium are used.

DE 2,132,547 describes a process for the hydrogenation of mononuclear or polynuclear aromatic diamines to produce the corresponding cycloaliphatic amines which is carried out in the presence of a suspended ruthenium catalyst.

EP 67,058 describes a process for the preparation of cyclohexylamine by catalytic hydrogenation of the corresponding aromatic amine. The catalyst used is ruthenium metal in a finely divided state on activated aluminum pellets. After four recyclings the catalyst began to lose its activity.

EP 324,984 relates to a process for the preparation of a mixture of optionally substituted cyclohexylamine and optionally substituted dicyclohexylamine by hydrogenation of optionally substituted aniline using a catalyst containing ruthenium and palladium on a support which, moreover, contains an alkaline reacting alkali metal compound acting as modifier. A basically similar process is described in EP 501,265, where the catalyst contains niobic acid, tantalic acid, or a mixture of the two, as modifier.

U.S. Pat. No. 2,606,925 describes a process for the preparation of an aminocyclohexyl compound by hydrogenation of a corresponding aromatic compound where a ruthenium catalyst is used, whose active catalytic component is selected from elementary ruthenium, ruthenium oxides, and ruthenium salts in which the ruthenium is present in the anion or in the cation. As revealed by the examples of said process, the catalyst is prepared and dried in a separate stage and is intoduced into the reaction vessel after a relatively long drying time.

A further process for the preparation of cyclohexylamine is described in U.S. Pat. No. 2,822,392, and the main feature of this patent specification involves the use of a specific reactor in which the aniline and hydrogen used as starting products are caused to react with each other countercurrently. U.S. Pat. No. 3,636,108 and U.S. Pat. No. 3,697,449 relate to the catalytic hydrogenation of aromatic compounds containing nitrogen using a ruthenium catalyst which additionally contains an alkali metal compound acting as modifier.

Common to all of the above processes is the use of mesoporous supports having surface areas (BET) which are typically between 50 and more than 1000 $m^2/g$ in order to achieve a high activity of the catalyst.

Furthermore, apart from the high cost of the catalyst, it has been found to be a disadvantage, particularly during hydrogenation using a rhodium-containing catalyst, that relatively large amounts of alkyl benzenes and other, unidentifiable compounds which are formed as decomposition products or by-products during hydrogenation frequently occur during such reactions. These by-products restrain working-up and purification of the reaction product particularly when alkylcyclohexanols are to be used, eg, as perfumes or for the preparation of perfumes. Furthermore, the activity of many catalysts used in the above processes declines rapidly, particularly when the hydrogenation is carried out for the acceleration of the reaction velocity at relatively high temperatures.

In a further embodiment thereof, the present invention relates to a process for reacting, preferably hydrogenating, polymers having groups to be reacted, preferably having nitrile groups by using a macroporous catalyst comprising ruthenium.

Processes for the hydrogenation of polymers comprising at least one unit to be hydrogenated are known as such. One group of polymers, which has been used in the past particularly intensively as starting materials in processes for hydrogenating polymers are polymers comprising nitrile groups. Also in the process according to the invention these polymers are preferably used leading to the corresponding polymers comprising amino groups.

The polymers having amino groups as obtained by this process may be used as e.g. branching agents, cross-linking agents or complexing agents, aming which as preferred applications for such polymers the paper manufacture, detergent industry, adhesives and cosmetics are exemplarily to be mentioned.

In the past a plurality of systems for the reduction of polymers comprising nitrile groups in order to obtain polymers comprising amino groups have been described. Among those also the hydrogenation by means of hydrogen has to be mentioned besides the reduction using complex metal hydrides, as e.g. described in the German patents DE 1 226 303 and DE 2 905 671.

The hydrogenation by means of hydrogen is significantly less expensive and—in contrast to the reduction by means of complex metal hydrides—only catalytic amounts of a metal containing component is required, which has economical and ecological advantages.

In the past, the hydrogenation by means of hydrogen was carried out either homogeneously catalyzed or heterogeneously catalyzed.

The homogeneous catalysis is chemically elegant, but the separation of the catalyst is significantly more elaborate compared to the heterogeneous catalysis. The use of a homogeneous catalyst is particularly disadvantageous in catalytic processes using polymers, since a distillative separation of the polymeric product from the catalyst is not possible. If the polymeric product is to be separated from the homogeneous catalyst by crystallization or precibitation, repeated crystallization is required, since inclusions of the catalyst occur, which leads to prolonged duration and higher costs.

Problems attributed to the separation of the catalyst do not occur in heterogeneous-catalyzed reactions. However, the known heterogeneous-catalyzed processes for the hydrogenation of polymers comprising nitrile groups, as carried out mostly by using metal solid bed catalysts according to Raney often only lead to poor yields and selectivities.

U.S. Pat. No. 2,456,428 describes the hydrogenation of poly(acrylonitrile), poly(methacrylonitrile) and similar polymers. After the hydrogenation in the presence of Raney nickel as a catalyst, none-reacted polymer has to be separated prior to the further work-up. Conclusively, the reaction described therein did not run quantitatively, the yields achieved by said process are poor.

According to U.S. Pat. No. 3,122,526, which relates to the hydrogenation of cyano-ethylated poly(acrylonitrile) by using Raney nickel as a catalyst, also only moderate yields of the corresponding amine of below 10% are obtained.

U.S. Pat. No. 2,585,583 describes the hydrogenation of copolymers of butadiene and acrylonitrile and methacrylonitrile, respectively, by using suspension hydrogenation catalysts. The U.S. Pat. No. 2,647,146 describes the hydrogenation of butadiene oligomers having nitrile end groups by using a mixture of two suspension catalysts (Pd on carbon and Ni on diatomaceous earth). According to these two processes the respectively used catalysts have to be separated from the reaction solution by filtration.

Summarizing the above, it has to be stated that the hydrogenation of polymers comprising nitrile groups in order to obtain polymers comprising amino groups is known as such, however, good yields of polymers comprising amino groups have been up to now only obtained by using suspension catalysts. However, these have to be separated from the reaction solution by filtration and may not be used in a solid bed reactor.

A catalyst consisting of a macroporous support material to which a Group VIIIB metal is applied, which can be used for the hydrogenation of carbon-carbon double bonds, is described in U.S. Pat. No. 5,110,779. Ninety percent of the pores that are present in the support material of the catalyst described in said reference possess a diameter of greater than 100 nm. The ratio of the surface area of the metal to that of the support is from 0.07 to 0.75:1. In said patent specification particularly emphasis is placed on the large surface area of the metal compared with that of the support, and this is stated to be surprising, since such a catalyst still possesses high activity.

Furthermore, the present invention relates in particular to a process for the reaction, preferably hydrogenation, of an organic compound comprising at least one C=group, such as a ketone, aldehyde, a carboxylic acid or a derivative thereof, or a mixture of two or more thereof.

It is thus an object of the present invention to provide a process for the reaction, preferably hydrogenation, of an organic compound as defined above where very high yields or almost quantitative conversions are achieved.

Another object of the invention is to provide such a process in which only a minimum content of by-products or decomposition products is formed during hydrogenation.

It should also be possible to carry out the process operating at high space velocities and with long on-stream times at an extremely high turnover number, the corresponding hydrogenation products being obtained in high yield and purity.

One or more of the above objects is/are achieved with a process for the reaction of an organic compound in the presence of a catalyst in which the active metal is ruthenium alone or together with at least one Group IB, VIIB, or VIIIB metal, applied to a support, where the support exhibits an average pore diameter of at least 50 nm and a surface area (BET) of not more than 30 m²/g and the amount of the active metal is from 0.01 to 30 wt.-% based on the total weight of the catalyst, wherein the ratio of the surface areas of the active metal and the catalyst support is <0.05.

The above objects and any other objects of the invention are achieved by means of hydrogenation processes as described in the sub-claims. One special advantage of the process of the invention is that very good results are attained when using only small metal contents in the catalyst.

Furthermore, the present invention relates to the catalyst as defined herein, i.e. a catalyst in which the active metal is ruthenium alone or together with at least one Group IB, VIIB, or VIIIB metal, applied to a support, where the support exhibits an average pore diameter of at least 50 nm and a surface area BET of not more than 30 m²/g and the amount of the active metal is from 0.01 to 30 wt.-% based on the total weight of the catalyst, and in which the ratio of the surface area of the active metal to that of the catalyst support is <0.05.

Furthermore, the process of the invention exhibits high turnover numbers at high space velocities over long catalyst on-stream times. The space velocity is the space-time yield of the process, ie the weight of the educt that is caused to react per unit of time per unit weight of the catalyst present. The "on-stream time" is the time during which that weight of educt is caused to react which can just be catalyzed by the catalyst without the latter suffering any change in properties and without the properties of the product being significantly modified.

COMPOUNDS

The term "organic compound" as used within the present invention comprises all organic compounds including low molecular weight (monomeric) and polymeric organic compounds which may be catalytically reacted, in particular those which exhibit groups which are treatable with hydrogen, such as C—C-double or C—C-triple bonds. This term comprises low molecular weight organic compounds as well as polymers. "Low molecular weight organic compounds" are compounds having a molecular weight of below 500. The term "polymer" is defined as relating to molecules having a molecular weight of higher than about 500.

The present invention relates particularly to a process for reacting an organic compound in the presence of a catalyst as defined herein, wherein the reaction is a hydrogenation, dehydrogenation, hydrogenolysis, aminating hydrogenation or dehalogenation, more preferably a hydrogenation.

In particular, organic compounds having one or more of the following structural units may be used:

  (I)

C=C

  (II)

C≡C

  (III)

C=N  (IV)

C≡N  (V)

C=O  (VI)

C=S  (VII)

—NO₂  (VIII)

The process of the invention is particularly suitable for reacting, preferably hydrogenating, an organic compound which is selected from the group consisting of an aromatic compound in which at least one hydroxyl group is bonded to an aromatic ring, an aromatic compound in which at least one amino group is bonded to an aromatic ring, a ketone, an aldehyde, a carboxylic acid or a derivative thereof, a polymer comprising at least one C—C double bond, a polymer comprising at least one C=O-group, a polymer comprising at least one C≡N-group, and a mixture of two or more thereof.

Within the process of the invention organic compounds comprising units of different structures, as defined above, may be reacted, such as organic compounds which exhibit C—C-multiple bonds and carbonyl groups, since the catalyst used within the process of the invention are capable to first selectively hydrogenate one of the two groups, i.e. to achieve a hydrogenation of these groups from about 90 to 100%, while at first the other groups are reacted, preferably hydrogenated, to an extent of less than 25% and in general 0 to about 7%. Generally, first the C—C-multiple bond and subsequently the C=O-group are reacted, e.g. hydrogenated, respectively.

The term "aromatic compound in which at least one hydroxyl group is bonded to an aromatic ring" or "aromatic compound in which at least one amino group is bonded to an aromatic ring" means all compounds which have a unit of the structure (I):

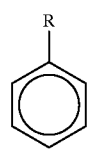  (I)

where R is a hydroxyl group or an amino group.

If, in the process of the present invention, use is made of aromatic compounds in which at least one hydroxyl group and also at least one unsubstituted or substituted $C_1$–$C_{10}$-alkyl radical and/or $C_1$–$C_{10}$-alkoxy radical is bonded to an aromatic ring, the resulting isomer ratio of cis to trans products can be varied within a wide range, depending on the reaction conditions (temperature, solvent). Furthermore, the compounds obtained can be processed further without further purification steps, since the formation of alkylbenzenes is virtually completely avoided.

Like the above-described compounds in which at least one hydroxyl group is bonded to an aromatic ring, aromatic compounds in which at least one amino group is bonded to an aromatic ring can also be hydrogenated by the process of the present invention to give the corresponding cycloaliphatic compounds with high selectivity. For the amines additionally substituted by a $C_1$–$C_{10}$-alkyl radical and/or $C_1$–$C_{10}$-alkoxy radical, what has been said above regarding the ratio of the cis and trans isomers also applies.

In particular, this embodiment virtually completely avoids the formation of deamination products such as cyclohexanes or partially hydrogenated dimerization products such as phenylcyclohexylamines.

In detail, the following compounds may be reacted with the process of the invention:

Aromatic compounds in which at least one hydroxyl group is bonded to an aromatic ring Aromatic compounds in which at least one hydroxyl group and preferably also at least one unsubstituted or substituted $C_1$–$C_{10}$-alkyl radical and/or alkoxy radical is bonded to an aromatic ring can be reacted, preferably hydrogenated, by means of the process of the present invention to give the corresponding cycloaliphatic compounds, with it also being possible to use mixtures of two or more of these compounds. The aromatic compounds used can be monocyclic or polycyclic aromatic compounds. The aromatic compounds contain at least one hydroxyl group bonded to an aromatic ring; the simplest compound of this group is phenol. The aromatic compounds preferably have one hydroxyl group per aromatic ring and can be substituted on the aromatic ring or rings by one or more alkyl and/or alkoxy radicals, preferably $C_1$–$C_{10}$-alkyl and/or alkoxy radicals, particularly preferably $C_1$–$C_{10}$-alkyl radicals, in particular methyl, ethyl, propyl, isopropyl, butyl, isobutyl and tert-butyl radicals; among the alkoxy radicals, preference is given to $C_1$–$C_8$-alkoxy radicals such as the methoxy, ethoxy, propoxy, isopropoxy, butoxy, isobutoxy and tert-butoxy radicals. The aromatic ring or rings and also the alkyl and alkoxy radicals may be unsubstituted or substituted by halogen atoms, in particular fluorine atoms, or other suitable inert substituents.

Preferably, the compounds which can be reacted, preferably hydrogenated, according to the present invention have at least one, preferably from one to four, in particular one, $C_1$–$C_{10}$-alkyl radical which is preferably located on the same aromatic ring as the hydroxyl group or groups. Preferred compounds are (mono)alkylphenols, where the alkyl radical can be in the o, m or p position relative to the hydroxyl group. Particular preference is given to trans-alkylphenols, also known as 4-alkylphenols, where the alkyl radical preferably has from 1 to 10 carbon atoms and is, in particular, a tert-butyl radical. Preference is given to 4-tert-butylphenol. Polycyclic aromatic compounds which can be used according to the present invention are, for example, β-naphthol and α-naphthol.

The aromatic compounds in which at least one hydroxyl group and preferably also at least one unsubstituted or substituted $C_1$–$C_{10}$-alkyl radical and/or alkoxy radical is bonded to an aromatic ring can also have a plurality of aromatic rings which are linked via an alkylene radical, preferably a methylene group. The alkylene group, preferably methylene group, which forms the linkage can have one or more alkyl substituents which can be $C_1$–$C_{20}$-alkyl radicals and are preferably $C_1$–$C_{10}$-alkyl radicals, particularly preferably methyl, ethyl, propyl, isopropyl, butyl or tert-butyl.

In these compounds, each of the aromatic rings can bear at least one bonded hydroxyl group. Examples of such compounds are bisphenols, which are linked in the 4 position via an alkylene radical, preferably a methylene radical.

In the process of the present invention, particular preference is given to reacting a phenol substituted by a $C_1$–$C_{10}$-alkyl radical, preferably $C_1$–$C_6$-alkyl radical, where the alkyl radical may be unsubstituted or substituted by an aromatic radical, or mixtures of two or more of these compounds.

In a further preferred embodiment of this process, p-tert-butylphenol, bis(p-hydroxyphenyl)dimethylmethane or a mixture thereof is reacted.

Aromatic compounds in which at least one amino group is bonded to an aromatic ring The process of the present invention also enables aromatic compounds in which at least one amino group is bonded to an aromatic ring to be reacted, preferably hydrogenated, to give the corresponding cycloaliphatic compounds, with mixtures of two or more of these compounds also being able to be used. The aromatic compounds can be monocyclic or polycyclic aromatic compounds. The aromatic compounds contain at least one amino group which is bonded to an aromatic ring. The aromatic compounds are preferably aromatic amines or diamines and can be substituted on the aromatic ring or rings or on the amino group by one or more alkyl and/or alkoxy radicals, preferably $C_1$–$C_{20}$-alkyl radicals, in particular methyl, ethyl, propyl, isopropyl, butyl, isobutyl and tert-butyl radicals. Among the alkoxy radicals, preference is given to $C_1$–$C_8$-alkoxy radicals such as methoxy, ethoxy, propoxy, isopropoxy, butoxy, isobutoxy and tert-butoxy radicals. The aromatic ring or rings and also the alkyl and alkoxy radicals can be unsubstituted or substituted by halogen atoms, in particular fluorine atoms, or other suitable inert substituents.

The aromatic compound in which at least one amino group is bonded to an aromatic ring can also have a plurality of aromatic rings which are linked via an alkylene group, preferably a methylene group. The alkylene group, preferably methylene group, which forms the linkage can bear one or more alkyl substituents which can be $C_1$–$C_{20}$-alkyl radicals and are preferably $C_1$–$C_{10}$-alkyl radicals, particularly preferably methyl, ethyl, propyl, isopropyl, butyl, sec-butyl or tert-butyl.

The amino group bonded to the aromatic ring may be unsubstituted or substituted by one or two of the above-described alkyl radicals.

Particularly preferred compounds are aniline, naphthylamine, diaminobenzenes, diaminotoluenes and bis-p-aminophenylmethane or mixtures thereof.

Compounds comprising C=O groups

Within the process of the invention it is also possible to react, in particular to hydrogenate, compounds comprising C=O groups, i.e. in particular aldehydes, ketones, carboxylic acids and their derivatives, such as carboxylic acid esters, carboxylic acid halides and carboxylic anhydrides, and mixtures of two or more of the above-mentioned compounds.

In particular aldehydes and ketones, preferably those having 1 to 20 C-atoms, such as formaldehyde, acetaldehyde, propionaldehyde, n-butyraldehyde, valeraldehyde, caproaldehyde, heptaldehyde, phenylacetaldehyde, acrolein, crotonaldehyde, benzaldehyde, o-, m-, p-tolualdehyde, salicylic aldehyde, anisaldehyde, vanillin, zinnamic aldehyde, acetone, methyl ethyl ketone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone, glycol aldehyde, glyoxal, 2,3-butandione, 2,4-pentandione, 2,5-hexandione, terephthalaldehyde, glutaraldehyde, diethylketone, methyl vinyl ketone, acetylacetone, 2-ethylhexanal, or mixtures of two ore more thereof, may be used.

Furthermore, also polyketones, such as copolymers of ethylene and CO are used.

Furthermore, carboxylic acids and derivatives thereof, preferably those having 1 to 20 C-atoms may be reacted. In particular, the following are to be mentioned:

Carboxylic acids, such as formic acid, acetic acid, propanoic acid, butanoic acid, iso-butanoic acid, n-valeric acid, pivalic acid, caproic acid, heptanoic acid, octanoic acid, decanoic acid, lauric acid, myristic acid, palmitic acid, stearic acid, acrylic acid, methacrylic acid, oleic acid, elaidic acid, linoleic acid, linolenic acid, cyclohexane carboxylic acid, benzoic acid, phenylacetic acid, o-, m-, p-toluylic acid, o-, p-chlorotenzoic acid, o-, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, teraphthalic acid, and mixtures of two or more thereof.

Carboxylic acid halides, such as the chlorides and bromides of the above-mentioned carboxylic acids, in particular acetylchloride or-bromide, stearic acid chloride or -bromide and benzoic acid chloride or -bromide, which are dehalogenated.

Carboxylic acid esters, such as the $C_1$- to $C_{10}$-alkyl esters of the above-mentioned carboxylic acids, particularly methyl formiate, acetic acid ester, butanoic acid butyl ester, dimethyl terephthalate, dimethyl adipate, methyl (meth) acrylate, butyrolactone, caprolactone and polycarboxylic acid esters, such as polyacrylic and polymethacrylic acid esters and copolymers and polyesters thereof, such as poly (methyl(meth)acrylates); these esters are in particular hydrogenated, i.e. the esters are reacted to the corresponding acids and alcohols.

Carboxylic anhydrides, such as anhydrides of the above-mentioned carboxylic acids, in particular acetic acid anhydride, propanoic acid anhydride, benzoic acid anhydride and maleic anhydride.

Carboxylic acid amides, such as amides of the above-mentioned carboxylic acids, such as formamide, acetamide, propionic amide, stearamide and terephthalamide.

In addition thereto, also hydroxy carboxylic acids, such as lactic, malic acid, tartaric acid or citric acid, or amino acids, such as glycine, alanine, proline and arginine may be reacted.

Nitriles

Furthermore, also nitriles, preferably aliphatic or aromatic mono or dinitriles, such as acetonitrile, propionitrile, butyronitrile, stearic acid nitrile, isocrotonic acid nitrile, 3-butinnitrile, 2,3-butadiene nitrile, 2,4-pentadiene nitrile, 3-hexene-1,6-dinitrile, chloracetonitrile, trichloracetonitrile, lactic acid nitrile, phenol acetonitrile, 2-chlorbenzonitrile, 2,6-dichlorobenzonitrile, isophthalonitrile, particularly aliphatic alpha, omega-dinitriles, such as succinonitrile, glutaronitrile, adiponitrile, pimelicnitrile and suberic nitrile or aminonitriles, such as 4-amino butanoic acid nitrite, 5-aminopentanoic acid nitrile, 6-aminohexanoic acid nitrite, 7-aminoheptanoic acid nitrite and 8-aminooctanoic acid nitrite.

Furthermore, within the process according to the invention, the following reactions may be carried out:

The hydrogenation of aromatic compounds, such as benzene, toluenes, xylols, naphthalines and substituted derivatives thereof, leading to the corresponding alicyclic compounds; the hydrogenation of alkenes or alkines, such as ethylene, propylene, 1-, 2-butene, 1-, 2-, 3- and 4-octene, butadiene, and hexatriene leading to the corresponding alkanes; the hydrogenation of nitroalkanes, such as nitroethane, nitromethane, nitropropane and 1,1-dinitroethane leading to the corresponding amines; the hydrogenation of imines, such as quinone imines, ketimines, ketene imines or aliphatic imines, such as propioamine, hexane imine; the dehalogenation of organic compounds which contain halogen atoms, particularly of aromatic halogen-containing compounds, such as chloro- and bromobenzene, bromo- and chlorotoluenes and chloro- and bromo xylols, also including compounds with more than one halogen atoms substituted, may be used; the aminating hydrogenation of i.e. alcohols, such as vinyl alcohol.

Furthermore, within the process of the invention also oximes may be reacted or secondary amines may be prepared starting from ketones and primary amines.

Polymers

The catalysts according to the invention may be also used for the hydrogenation, dehydrogenation, hydrogenolysis, aminating hydrogenation and dehalogenation of large molecules, preferably of polymers.

Accordingly, the present invention also relates to a process for reacting a polymer comprising at least one catalytically reactable group in the presence of the above identified catalyst, wherein the hydrogenation of polymers comprising C=O-groups, such as polyesters of dicarboxylic acids, unsaturated monocarboxylic acids, such as poly(meth)acrylates, olefin/CO-copolymers or polyketones, and the hydrogenation of polymers comprising nitrile groups, such as copolymers of styrene and butadiene, copolymers of acrylonitrile and the aminating hydrogenolysis of polyvinylalcohols and polyketones in the presence of the above-mentioned catalyst are preferred.

In particular, the present invention relates to a process for the hydrogenation of a polymer comprising at least one C=O-group or a polymer comprising at least one C≡N-group.

The term "polymer comprising at least one catalytically reactable group" relates to all polymers comprising such groups, in particular to polymers comprising units having the structures (I) to (VIII), as defined above with respect to the monomeric compounds, or a halogen atom. Needless to say that the referenced polymers comprise the respective unit at least once and that also one or more units of two or more of said structures may be present in the polymer reacted according to the invention.

The average molecular weight of the polymers to be reacted within the process of the invention is generally about 500 to about 500000, preferably about 1000 to about 100000 and more preferably about 1000 to about 50000. It is, however, possible to also react polymers having a higher molecular weight of up to one or several millions.

As examples for polymers which are to be reacted, preferably hydrogenated, with the process of the invention, the following are to be mentioned:

Polymers having C—C-double bonds, e.g. polybutadienes, such as poly(2,3-dimethylbutadiene), polyisoprene, polyacetylenes and polycylopenta- and -hexadiene; polymers having C—C-triple bonds, such as polydiacetylenes; polymers having aromatic groups, such as polystyrene, terpolymers of acrylonitrile, butadiene and styrene, and copolymers of styrene and acrylonitrile; polymers having C—N-triple bonds, such as polyacrylonitrile, polyacrylonitrile-copolymers with e.g. vinyl chloride, vinylidene chloride, vinyl acetate or (meth)acrylic acid esters or mixtures of two or more thereof as comonomers; polymers having C—O-double bonds, such as polyesters, polyacrylamides, poly(acrylic acids), polyurea and polyketones; polymers having C—S-double bonds, such as polysulfones and polyethersulfones; halogen-containing polymers, such as poly(vinyl chloride) and poly(vinylidene chloride); and polymers containing nitro groups, which may be obtained by nitration of e.g. polyolefins by means of polymer analogous reactions.

Examples for polymers being preferably used within the present invention include polyisoprene, polybutadiene, ethylene/CO-copolymers, propylene/CO-copolymers, poly(methyl(meth) acrylate), polyterephthalate, polyadipate, styrene-butadiene-copolymers, acrylonitrile-butadiene-copolymers, acrylonitrile-styrene-copolymers, styrene-isoprene-styrene-triblockcopolymers, styrene-butadiene-styrene-triblockcopolymers and styrene-butadiene-styrene-starblockcopolymers.

Generally, a complete reaction of the introduced educts is achieved. However, the reaction, preferably hydrogenation, may be also carried out in such a way that by suitably choosing temperature, e.g. $H_2$-pressure and $H_2$-amount only one kind of e.g. groups to be hydrogenated may be reacted, while the other kind of e.g. groups to be hydrogenated are not hydrogenated.

The process of the invention is particularly suitable for reacting, preferably hydrogenating, polymers comprising units of different structure, as defined above, e.g. a polymer comprising C—C-multiple bonds and C=O-groups and/or C≡N-groups, since the catalyst of the present invention is capable to first selectively react the C—C multiple bond, e.g. to achieve a hydrogenation of these groups of about 90 to 100%, while at the same time the C=O-groups and/or C≡N-groups are reacted, e.g. hydrogenated to an extent of less than 25% and in general 0 to about 7%.

After finishing this reaction, preferably hydrogenation of the C—C-multiple bonds, it is of course possible to nearly quantitatively react, preferably hydrogenate, the other unsaturated groups being present in the polymer, e.g. C=O-groups by further introducing hydrogen.

The process of the invention may be used for already isolated and living polymers.

CATALYSTS

The catalysts used in the process of the invention can be manufactured industrially by applying ruthenium and optionally at least one Group IB, VIIB, or VIIIB metal to a suitable support, said additional metal being different from Ru.

Application may be effected by impregnating the support in aqueous metal salt solutions, such as aqueous ruthenium salt solutions, by spraying corresponding metal salt solutions on to the support, or by other suitable methods. Suitable ruthenium salts for the preparation of the ruthenium salt solutions and suitable Group IB, VIIB, or VIIIB metal salts are the nitrates, nitrosylic nitrates, halides, carbonates, carboxylates, acetyl acetonates, chlorine complexes, nitro complexes or amine complexes of the corresponding metals, the nitrates and nitrosylic nitrates being preferred.

In the case of catalysts containing not only ruthenium but also other metals applied, as active metal, to the support, the metal salts or metal salt solutions may be applied simultaneously or successively.

The supports that are coated or impregnated with the ruthenium salt solution or said other metal salt solution are subsequently dried, preferably at temperatures ranging from 100° C. to 150° C., and optionally calcined at temperatures ranging from 200° to 600° C., preferably from 350° to 450° C. When impregnation is carried out in separate stages the catalyst is dried and optionally calcined after each impregnation step, as described above. The order in which the active components are applied by impregnation is arbitrary.

The coated and dried and optionally calcined supports are then activated by treatment in a gas stream containing free hydrogen at temperatures ranging from about 30° to about 600° C. and preferably from about 150° to about 450° C. The gas stream preferably consists of from 50 to 100 vol % of $H_2$ and from 0 to 50 vol % of $N_2$.

If not only ruthenium but also one or more other Group IB, VIIB, or VIIIB metals are applied to the support, platinum, copper, rhenium, cobalt, and nickel or mixtures of two or more thereof are preferably used.

The ruthenium salt solution or said other metal salt solution is applied to the support(s) in such quantity that the total content of active metal, based, in each case, on the total weight of the catalyst, is from about 0.01 to about 30 wt.-%, preferably from about 0.01 to about 5 wt.-%, and more preferably from about 0.01 to about 1 wt.-%, particularly from about 0.05 to about 1 wt.-%.

The total surface area of the metal on the catalyst is preferably from about 0.01 to about 10 $m^2/g$, more preferably from about 0.05 to about 5 $m^2/g$, and very preferably from about 0.05 to about 3 $m^2/g$, of the catalyst. The metal surface area is determined by the chemisorption methods described by J. LeMaitre et al in Characterization of Heterogenous Catalysts, Ed. Francis Delanney, Marcel Dekker, New York 1984, pp. 310–324.

In the catalyst that is used in the process of the invention the ratio of the surface area of the active metal(s) to that of the catalyst support is about 0.05 or less, where the lower limit is about 0.0005.

SUPPORTS

The support materials that can be used for the manufacture of the catalysts employed in the process of the invention are those which are macroporous and exhibit an average pore diameter of at least about 50 nm, preferably at least about 100 nm, more preferably at least about 500 nm, and whose surface area (BET) is not more than about 30 $m^2/g$, preferably not more than about 15 $m^2/g$, more preferably not more than about 10 $m^2/g$, very preferably not more than about 5 $m^2/g$, and most preferably not more than about 3 $m^2/g$. More specifically, the average pore diameter of the support is preferably from about 100 nm to about 200 mmm and more preferably from about 500 nm to about 50 mmm. The surface area of the support is preferably from about 0.2 to about 15 $m^2/g$, more preferably from about 0.5 to about 10 $m^2/g$, very preferably from about 0.5 to about 5 $m^2/g$, and most preferably from about 0.5 to about 3 $m^2/g$.

The term "macroporous" is used in the present description as defined in Pure Applied Chem. 45, pp. 79, (1976), namely to designate pores having diameters greater than 50 nm. The surface area of the support is determined by the BET method by $N_2$ adsorption, in particular as specified in DIN 66,131. Determination of the average pore diameter and pore size distribution is carried out by Hg porosymmetry, in particular as specified in DIN 66,133.

Preferably the pore size distribution of the support can be approximately bimodal, where a pore size distribution showing maximum values at approximately 600 nm and approximately 20 mmm in the case of bimodal distribution form a special embodiment of the invention.

More preferably, the support has a surface area of 1.75 m²/g and exhibits said bimodal distribution of pore diameters. The pore volume of this preferred support is preferably equal to about 0.53 ml/g.

Macroporous support materials which can be used are for example activated charcoals, silicon carbide, aluminum oxide, silicon dioxide, titanium dioxide, zirconium dioxide, magnesium oxide, zinc oxide, or mixtures of two or more thereof, aluminum oxide and zirconium dioxide being preferably used. The catalysts used in the process of the invention show a high reactivity (high turnover number), selectivity and on-stream time. Using the catalysts proposed for use in the process of invention there are obtained, in hydrogenations, hydrogenation products in high yield and purity, subsequent purification being unnecessary.

In the hydrogenation of an aromatic compound in which at least one hydroxyl group is attached to an aromatic core, there are obtained, particularly in the hydrogenation of 4-alkyl-substituted or 4-alkoxy-substituted phenols, as described above, predominantly trans cycloaliphatic compounds. The content of trans cycloaliphatic compounds is, according to one embodiment of the invention, at least 60% and is preferably at least 65%. The conversion is virtually quantitative, the residual aromatic content is preferably less than 0.01 wt.-%, based on the total weight of the product. The hydrogenation product thus obtained can, in a preferred embodiment of the present invention, be directly passed to further processing, without having to be purified.

SOLVENTS OR DILUENTS

In the process of the invention reaction, preferably hydrogenation, can be carried out in the absence of a solvent or diluent, i.e. it is not necessary to carry out the reaction in solution.

It is also possible to directly react the polymer in its melt.

Preferably however a solvent or diluent is used. The solvents or diluents used can be any suitable solvents or diluents. The choice thereof is not crucial. For example, the solvents or diluents can contain small amounts of water, if desired.

In the reaction, preferably hydrogenation, of an aromatic compound in which at least one hydroxyl group is attached to an aromatic core, examples of suitable solvents or diluents include the following:

Straight-chain or cyclic ethers, such as tetrahydrofuran or dioxane, and also aliphatic alcohols in which the alkyl radical exhibits preferably from 1 to 10 carbon atoms and more preferably from 3 to 6 carbon atoms.

Examples of alcohols to be preferably used are isopropanol, n-butanol, isobutanol and n-hexanol. Mixtures of these or other solvents or diluents may also be used.

In the reaction, preferably hydrogenation, of an aromatic compound in which at least one amino group is attached to an aromatic core, examples of suitable solvents or diluents include the following:

Straight-chain or cyclic ethers, such as tetrahydrofuran or dioxane, and also ammonia and monoalkylamines or dialkylamines in which the alkyl radical exhibits preferably from 1 to 3 carbon atoms, such as methylamine, ethylamine, or propylamine, or the corresponding dialkylamines.

Mixtures of these or other solvents or diluents may also be used.

In both of the above embodiments, the amount of the solvent or diluent used is not subject to particular restrictions and can be freely selected as required, but those amounts are preferred which produce a 10 to 70 wt.-% strength solution of the compound to be hydrogenated.

When carrying out the process of the invention it is particularly preferred that the product that is formed in the reaction, preferably hydrogenation of this process be used as solvent, optionally together with other solvents or diluents. In this case a portion of the product that is formed in the process can be mixed with the compounds to be reacted, preferably hydrogenated. The weight of hydrogenation product admixed as solvent or diluent is preferably from 1 to 30 times, more preferably from 5 to 20 times and most preferably from 5 to 10 times the weight of the aromatic compounds to be reacted, preferably hydrogenated.

The above may also be applied for the other compounds which are reacted according to the invention. Also in this respect no limitation with regard to the solvent and diluent exists.

In the reaction of polymers examples of suitable solvents or diluents include the following:

hydrocarbons, such as hexane, cyclohexane, methylcyclohexane, heptane, octane, toluene, xylene, etc., and straight-chain or cyclic esters, such as tetrahydrofurane, dioxane, dibutylether, methyl-tert.-butylether, etc., ketones, such as methyl ethyl ketone and acetone, esters, such as ethylacetate, or amides, such as DMF and N-methylpyrrolidon.

Preferably used are cyclohexane, toluene or THF. Mixtures of these and other solvents and diluents may also be used.

If the polymer was obtained by solution polymerization, it is also possible to direct react the obtained solution comprising the polymer within the process according to the invention.

The amount of the used solvent or diluent is not particularly limited within the process according to the invention and may be freely chosen according to demand. However, such amounts are preferred which lead to a solution comprising 1 to 70, preferably 1 to 40 wt.-% of the polymer to be reacted.

REACTION

In the following the reaction is described by means of a hydrogenation as an example, wherein—in case a dehydrogenation or an oxidation is carried out—instead of hydrogen or hydrogen-containing gases gaseous hydrocarbons or oxygen-containing gases may be used under the below-described conditions.

The hydrogenation is carried out at suitable pressures and temperatures. Pressures above about $2 \cdot 10^6$ Pa, preferably above $5 \cdot 10^6$ Pa and particularly pressures of from about $1 \cdot 10^7$ to about $3 \cdot 10^7$ Pa are preferred. Preferred temperatures range from about 30° to about 250° C. and are preferably about 100° to about 220° C. and particularly about 150° to about 200° C.

The hydrogenation process can be carried out continuously or batchwise. When the process is carried out continuously a portion of the hydrogenation product leaving the reactor can be added the reactor feed upstream of the reactor. An portion of the hydrogenation product leaving the reactor is recycled as solvent, such that the proportions given under the heading "Solvents and Diluents" are attained. The remaining amount of hydrogenation product is retrieved.

When the process is carried out continuously the feed rate of the compound(s) to be hydrogenated is preferably from about 0.05 to about 3 kg per liter of catalyst per hour and more preferably from about 0.1 to about 1 kg per liter of catalyst per hour.

The hydrogenating gases used can be arbitrary gases containing free hydrogen and exhibiting no harmful amounts of catalyst poisons, such as CO. For example, reformer exhaust gases can be used. Pure hydrogen is preferably used as hydrogenating gas.

In the case of phenols and amines additionally substituted by at least one optionally substituted $C_1$–$C_{10}$ and/or alkoxy radical the isomer ratio of cis-configured to trans-configured products obtained can be varied over a wide range by varying the reaction conditions (temperature, solvents).

If an aromatic compound in which at least one amino group is attached to an aromatic core is to be hydrogenated using the catalyst defined above the hydrogenation can also be carried out in the presence of ammonia or dialkylamines, for example methylamine, ethylamine, propylamine or dimethylamine, diethylamine or dipropylamine. Suitable amounts of ammonia or monoalkylamine or dialkylamine are used, these preferably being from about 0.5 to about 50 parts by weight, more preferably from about 1 to about 20 parts by weight, based, in each case, on 100 parts by weight of the compound(s) to be hydrogenated. Anhydrous ammonia or anhydrous amines are particularly preferably used.

For oxidations generally air or pure oxygen is used. For dehydrogenations usually carbohydrates, particularly methane or natural gas, are used.

The invention is described in detail below with reference to some embodiments, where Examples 1 to 4 refer to the hydrogenation of an aromatic compound in which at least one hydroxyl group is attached to an aromatic core, and Examples 5 to 7 relate to the hydrogenation of an aromatic compound in which at least one amino group is attached to an aromatic core. Examples 8 to 12 relate to the reaction of compounds comprising C=O-groups, and Examples 13 and 14 relate to the reaction of polymers.

EXAMPLES

Preparation of catalyst 1

A macroporous aluminum oxide support in the form of 3–6 mm pellets having a surface area (BET) of 10 $m^2$/g, a pore volume of 0.45 m l/g and a pore diameter of 210 nm, was impregnated with an aqueous ruthenium(III) nitrate solution. The volume of solution absorbed by the support was approximately equivalent to the pore volume of the support used.

The support impregnated with the ruthenium(III) nitrate solution was then dried at a temperature of 120° C. and reduced in a stream of hydrogen at a temperature of 200° C. The catalyst thus prepared contained 0.5 wt.-% of ruthenium based on the total weight of the catalyst and had a ruthenium surface area of 0.5 $m^2$/g, which was determined by $H_2$ pulsed chemisorption (pulsed Chemisorp 2700, 35° C.). The ratio of the surface area of the metal to that of the support was 0.05.

Example 1

A 50 wt.-% strength solution of p-tert-butylphenol was prepared in THF. Then 2500 g /h of this solution were passed with hydrogen at a temperature of 180° C. and an overall pressure of 2.6·$10^7$ Pa through a flow reactor, which was packed with 3.2 L of the Ru catalyst described above. Following removal of the solvent, by distillation, the hydrogenation product had the following composition:

99.9% of cis,trans-4-tert-butylcyclohexanol
<0.01% of p-tert-butylphenol

Example 2

The hydrogenation was carried out as described in Example 1 except that 3500 g of the 50 wt.- % p-tert-butylphenol solution in THF were passed through the reactor at a temperature of 200° C. Following distillation of the solvent, the hydrogenation product possessed the following composition:

99.8% of cis,trans-4-tert-butylcyclohexanol
<0.01% of p-tert-butylphenol

Example 3

The hydrogenation was carried out as described in Example 1 except that a 50 wt.-% solution of p-tert-butylphenol in isobutanol was used. Following the distillation of the solvent, the hydrogenation product possessed the following composition:

67.5% of trans4-tert-butylcyclohexanol
32.4% of cis4-tert-butylcyclohexanol
<0.01% of p-tert-butylphenol

Example 4

In an autoclave having a capacity of 3.5 L 2 kg of a solution of 50 wt.-% of bisphenol A in THF and 500 m l of the macroporous catalyst of Example 1 (0.4 wt.-% of Ru on $Al_2O_3$) were placed in a catalyst basket. Hydrogenation was then carried out at a temperature of 150° C. and under a pressure of 2·$10^7$ Pa over a period of five hours batchwise. The conversion to the desired cycloaliphatic mixture of diol isomers was quantitative, and the residual aromatics content was less than 0.01%.

Example 5

1.2 L of the catalyst prepared as described above were packed into an electrically heated flow reactor. The hydrogenation of aniline was then commenced under a pressure of 2·$10^7$ Pa and at a temperature of 160° C. without previous activation.

The hydrogenation was carried out continuously in ascending mode, a portion of the hydration effluent being recycled via a circulating pump and added to the starting material upstream of the reactor. The amount of hydrogenation product added as solvent was thus ten times that of the aniline. At the head of the separator from 500 to 600 L of $H_2$/h were depressurized. The amount of aniline that was continuously fed to the reactor corresponded gave a space velocity of 1.0 kg/L·h.

As a function of reaction temperature the following product compositions were attained under steady-state reaction conditions:

| Temperature (°C.) | CHA[1] (%) | DCHA[2] (%) | Aniline (%) | Cyclohexane + Cyclohexene (%) |
|---|---|---|---|---|
| 160 | 99.1 | 0.45 | 0.10 | 0.04 |
| 180 | 97.0 | 2.75 | 0.06 | 0.06 |
| 200 | 95.9 | 3.9 | — | — |

[1]CHA = cyclohexylamine;
[2]DCHA = dicyclohexylamine

Example 6

The hydrogenation was carried out as described in Example 5 except that additionally anhydrous ammonia was continuously metered in. Based on 100 wt.-% of aniline 10 parts by weight of ammonia were added. As a function of reaction temperature the following product compositions were attained under steady-state reaction conditions:

| Temperature (°C.) | CHA[1] (%) | DCHA[2] (%) | Aniline (%) | Cyclohexane + Cyclohexene (%) |
|---|---|---|---|---|
| 180 | 99.3 | 0.08 | — | 0.07 |
| 200 | 98.4 | 0.8 | — | 0.09 |

[1]CHA = cyclohexylamine;
[2]DCHA = dicyclohexylamine

Example 7

In an autoclave having a capacity of 3.5 L there were placed 2 kg of a solution of 50 wt.-% of toluylene diamine (mixture of 2.4-;2.6-diaminotoluene isomers) in THF and 500 ml of the catalyst that was described above. Hydrogenation was then carried out at a temperature of 150° C. and under a pressure of $2 \cdot 10^7$ Pa over a period of five hours batchwise. The conversion to the desired cycloaliphatic mixture of diamine isomers was quantitative, and the residual aromatics content was less than 0.01 %.

Example 8

3 l of catalyst 1 were introduced into a tube reactor (length=2500 nm, dia=45 nm. Subsequently, the reactor was filled with n-butanol and was heated to 180° C. at a hydrogen pressure of $3 \cdot 10^6$ Pa (30 bar). Then, an amount of 1 kg/h n-butylalderhyde was continuously introduced into the reactor with a flow amount of 50 l/h. The obtained reaction product was colorless and free from ruthenium.

A conversion of 99.4% and a selectivity with respect to n-butanol of 99.7, respectively based on the introduced amount of n-butylalderhyde, was determined by gas chromotagraphic evaluation.

Example 9

3 l of catalyst 1, 700 g of a copolymer of ethylene and CO ($M_w$ 5000, CO content 35% percent), dissolved in 1300 g THF, were introduced in a 3.5l-autoclav.

Subsequently, the mixture was hydrogenated at 180° C. and $2 \cdot 10^7$ Pa (200 bar) hydrogen pressure for 5 hours. The conversions to the desired polyalcohol was 93%, based on the introduced amount of the copolymer.

Example 10

3 l of catalyst 1 were introduced into a 3.5l-autoclav, and 2000 g benzaldehyde were introduced there into. Subsequently the mixture was hydrogenated at 180° C. and $2 \cdot 10^7$ Pa (200 bar) hydrogen pressure for 10 hours. The conversion to the desired cyclohexyl methanol was 100% at a selectivity of 96.5%, based on the introduced amount of benzaldehyde, respectively.

Example 11

3 l of catalyst 1 were introduced into a 3.5l-autoclav, and 2000 g 2-ethylhexanaol were introduced there into. Subsequently, the mixture was hydrogenated at 180° C. and $2 \cdot 10^7$ Pa (200 bar) hydrogen pressure for 10 hours. The conversion to the desired 2-ethylhexanol was 100% at a selectivity of 97.2%, based on the introduced amount of 2-ethylhexanol, respectively.

Example 12

In a 0.3l-stirring autoclav, 100 ml adipodimethylester was reacted at catalyst 1. The mixture was stirred for 12 hours at a hydrogen pressure of $2 \cdot 10^7$ Pa (200 bar) and a temperature of 220° C. A conversion of 98% and a yield with respect to hexandiol of 91% based on the introduced amount of adipodimethylester was determined by a gaschromatic analysis of the obtained product.

Example 13

Preparation of catalyst 2

A macroporous aluminum oxide support in the form of 3–6 mm pellets having a surface area (BET) of 10 m²/g, a pore volume of 0.45 m l/g and a pore diameter of 210 nm, was impregnated with an aqueous ruthenium(III) nitrate solution. The volume of solution absorbed by the support was approximately equivalent to the pore volume of the support used.

The support impregnated with the ruthenium(III) nitrate solution was then dried at a temperature of 120° C. and reduced in a stream of hydrogen at a temperature of 200° C. The catalyst thus prepared contained 0.3 wt.-% of ruthenium based on the total weight of the catalyst and had a ruthenium surface area of 0.4 m²/g, which was determined by $H_2$ pulsed chemisorption (pulsed Chemisorp 2700, 35° C). The ratio of the surface area of the metal to that of the support was 0.05.

Hydrogenation 100 g of a solution of 15 wt.-% of an acrylonitrile-butadiene-copolymer containing 18 wt.-% acrylonitrile and having an average molecular weight of 3.000 in THF, 60 ml ammonia and 15 g catalyst 2 were introduced into a 300 ml autoclav.

The nitrile conversion was 92%. No degradation of the molecular weight took place.

Example 14

Preparation of catalyst 3

A macroporous aluminum oxide support in the form of 3–6 mm pellets having a surface area (BET) of 10 m²/g, a pore volume of 0.45 m l/g and a pore diameter of 210 nm, was impregnated with an aqueous ruthenium(III) nitrate solution. The volume of solution absorbed by the support was approximately equivalent to the pore volume of the support used.

The support impregnated with the ruthenium(III) nitrate solution was then dried at a temperature of 120° C. and reduced in a stream of hydrogen at a temperature of 200° C. The catalyst thus prepared contained 0.2 wt.-% of ruthenium based on the total weight of the catalyst and had a ruthenium surface area of 0.3 m²/g, which was determined by $H_2$ pulsed chemisorption (pulsed Chemisorp 2700, 35° C.). The ratio of the surface area of the metal to that of the support was 0.03.

Hydrogenation 100 g of a solution of 15 wt.-% of an acrylonitrile-butadiene-copolymer containing 18 wt.-% acrylonitrile and having an average molecular weight of 3.000 in THF, 60 ml ammonia and 15 g catalyst 3 were introduced into a 300 ml autoclav.

The nitrile conversion was 90%. No degradation of the molecular weight took place.

We claim:

1. A process for the reaction of an organic compound in the presence of a catalyst in which the active metal is ruthenium alone or together with at least one Group IB, VIIB, VIIIB metal, applied to a support; wherein the support exhibits an average pore diameter of a least 50 nm and a surface area BET of not more than 30 m$^2$/g and the amount of the active metal is from 0.01 to 30 wt % based on the total weight of the catalyst; and wherein the ratio of the surface area of the active metal to that of the catalyst support is <0.05: and wherein the organic compound is selected from the group consisting of an aromatic compound in which at least one hydroxyl group is bonded to an aromatic ring;

an aromatic compound in which at least one amino group is bonded to an aromatic ring, a ketone, an aldehyde, a carboxylic acid or a derivative thereof;

a polymer comprising at least one C—C double bond; and a polymer comprising at least one C—N-triple bond; or a mixture of two or more thereof.

2. A process according to claim 1, wherein said Group IB, VIIB, or VIIIB metal is platinum, copper, rhenium, cobalt, nickel or a mixture of two or more thereof.

3. A process according to claim 1, wherein the support exhibits a surface area (BET) of not more than 15 m$^2$/g.

4. A process according to claim 1, wherein the content of active metal is from 0.01 to 1 wt % based on the total weight of the catalyst.

5. A process according to claim 1, wherein the average pore diameter of the support is least 100 nm.

6. A process according to claim 1, wherein the support is activated charcoal, silicon carbide, aluminum oxide, silicon dioxide, titanium dioxide, zirconium dioxide, magnesium oxide, zinc oxide, or a mixture of two or more thereof.

7. A process according to claim 1, wherein the reaction is a hydrogenation, a dehydrogenation, a hydrogenolysis, an aminating hydrogenation or a dehalogenation.

8. A process according to claim 1, wherein the reaction is carried out in the presence a solvent or diluent.

\* \* \* \* \*